US00PP14569P29

(12) United States Plant Patent

Kearley et al.

(10) Patent No.: US PP14,569 P2
(45) Date of Patent: Mar. 2, 2004

(54) LANTANA PLANT NAMED 'RED BUTLER'

(50) Latin Name: *Lantana camara*
Varietal Denomination: Red Butler

(75) Inventors: Mary E. Kearley, Hawthorne, FL (US); Richard C. Kearley, Jr., Hawthorne, FL (US)

(73) Assignee: Robrick Nursery Inc., Hawthorne, FL (US)

( * ) Notice: Subject to any disclaimer, the term of this patent is extended or adjusted under 35 U.S.C. 154(b) by 0 days.

(21) Appl. No.: 10/408,181

(22) Filed: Apr. 6, 2003

(51) Int. Cl.[7] ..... A01H 5/00
(52) U.S. Cl. ..... Plt./227
(58) Field of Search ..... Plt./227

*Primary Examiner*—Kent Bell
(74) *Attorney, Agent, or Firm*—C. A. Whealy

(57) ABSTRACT

A distinct cultivar of Lantana plant named 'Red Butler', characterized by its upright and outwardly spreading plant habit; freely flowering habit; and large inflorescences with red-colored flowers.

2 Drawing Sheets

Botanical classification/cultivar designation: *Lantana camara* cultivar Red Butler.

BACKGROUND OF THE INVENTION

The present Invention relates to a new and distinct cultivar of Lantana plant, botanically known as *Lantana camara*, and hereinafter referred to by the cultivar name Red Butler.

The new Lantana is a product of a planned breeding program conducted by the Inventors in Hawthorne, Fla. The objective of the breeding program is to create compact Lantanas with red-colored flowers.

The new Lantana originated from a cross made by the Inventors in August, 2000 of the Lantana cultivar Dallas Red, not patented, as the female, or seed parent, with an unidentified Lantana selection as the male, or pollen parent. The new Lantana was selected as a single plant from the resulting progeny by the Inventors in a controlled environment in Hawthorne, Fla., on Jun. 30, 2001, on the basis of its growth habit and attractive flower coloration.

Asexual reproduction of the new cultivar by terminal cuttings taken in a controlled environment in Hawthorne, Fla., since Jun. 30, 2001, has shown that the unique features of this new Lantana are stable and reproduced true to type in successive generations.

SUMMARY OF THE INVENTION

Plants of the cultivar Red Butler have not been observed under all possible environmental conditions. The phenotype may vary somewhat with variations in environment and culture such as temperature and light intensity, without however, any variance in genotype.

The following traits have been repeatedly observed and are determined to be the unique characteristics of 'Red Butler'. These characteristics in combination distinguish 'Red Butler' as a new and distinct Lantana cultivar:

1. Upright and outwardly spreading plant habit.
2. Freely flowering habit.
3. Large inflorescences with red-colored flowers.

Plants of the new Lantana can be compared to plants of the female parent, the cultivar Dallas Red. In side-by-side comparisons conducted in Hawthorne, Fla., plants of the new Lantana differed from plants of the cultivar Dallas Red in the following characteristics:

1. Plants of the new Lantana were more compact than plants of the cultivar Dallas Red.
2. Plants of the new Lantana had smaller leaves than plants of the cultivar Dallas Red.
3. Plants of the new Lantana had larger inflorescences than plants of the cultivar Dallas Red.
4. Plants of the new Lantana had red-colored flowers whereas plants of the cultivar Dallas Red had red, orange and yellow-colored flowers.

Plants of the new Lantana differ from plants of the male parent, the unidentified Lantana selection, primarily in the new Lantana's unique combination of flower coloration, and freely-flowering habit.

Plants of the new Lantana can be compared to plants of the cultivar Radiation, not patented. In side-by-side comparisons conducted in Hawthorne, Fla., plants of the new Lantana differed from plants of the cultivar Radiation in the following characteristics:

1. Plants of the new Lantana were more upright and not as mounding as plants of the cultivar Radiation.
2. Leaves of plants of the new Lantana were lighter green in color than leaves of plants of the cultivar Radiation.
3. Plants of the new Lantana had larger inflorescences than plants of the cultivar Radiation.
4. Plants of the new Lantana had red-colored flowers whereas plants of the cultivar Radiation had orange and orange red-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Lantana.

The photograph on the first sheet comprises a side perspective view of a typical flowering plant of 'Red Butler' grown in a container.

The photograph on the second sheet comprises a close-up view of typical inflorescences and leaves of 'Red Butler'.

DETAILED BOTANICAL DESCRIPTION

In the following description, color references are made to The Royal Horticultural Society Colour Chart, 1995 Edition, except where general terms of ordinary dictionary significance are used. Plants used for the photographs and description were planted in two-gallon containers after rooting and grown for about three months during the spring in a polyethylene-covered greenhouse in Hawthorne, Fla. During the production of the plants in the greenhouse, day temperatures ranged from 18 to 38° C. and night temperatures ranged from 8 to 20° C.

Botanical classification: *Lantana camara* cultivar Red Butler.

Parentage:

*Female parent.*—*Lantana camara* cultivar Dallas Red, not patented.

*Male parent.*—Unidentified *Lantana camara* selection, not patented.

Propagation:

*Type cutting.*—Terminal cuttings.

*Time to initiate roots, summer.*—About 10 days at 30° C.

*Time to initiate roots, winter.*—About 14 days at 24° C.

*Time to develop roots, summer.*—About 30 days at 30° C.

*Time to develop roots, winter.*—About 35 days at 24° C.

*Root description.*—Fibrous; initially white in color then becoming closer to 156B with development.

*Rooting habit.*—Freely branching; dense.

Plant description:

*Form.*—Flowering subshrub; upright and outwardly spreading. Freely branching; typically about two lateral branches potentially forming at every node; pinching enhances lateral branch development.

*Plant height.*—About 80 cm.

*Plant diameter.*—About 75 cm.

*Vigor.*—Vigorous, rapid growth rate.

*Lateral branches.*—Length: About 25 cm. Diameter: About 5 mm. Internode length: About 5 cm. Strength: Strong, but flexible. Texture: Rough, coarse pubescence. Color: 144B.

*Foliage description.*—Leaves simple, generally symmetrical and long-persisting; opposite. Length: About 6 to 10 cm. Width: About 5 to 6 cm. Shape: Lanceolate to ovate. Apex: Acute. Base: Attenuate. Margin: Crenate to serrate with ciliation. Texture, both surfaces: Leathery, rough, coarse; pubescent. Venation pattern: Pinnate, arcuate. Color: Developing foliage, upper surface: 137A. Developing foliage, lower surface: 137C. Fully expanded foliage, upper surface: 141A. Fully expanded foliage, lower surface: 138A. Venation, upper surface: 146B. Venation, lower surface: 138D. Petiole length: About 2 to 2.6 cm. Petiole diameter: About 3 mm. Petiole texture, both surfaces: Pubescent. Petiole color, upper and lower surfaces: 138B.

Flower description:

*Flower type and habit.*—Small salverform flowers arranged in axillary umbels; flowers face mostly upward or outward. Flowers self-cleaning. Very freely flowering with potentially two inflorescences per node; typically about 20 to 30 flowers per umbel.

*Natural flowering season.*—Spring until frost in the autumn; flowering continuous during the flowering period.

*Flower longevity on the plant.*—About one week.

*Fragrance.*—Very faint; spicy.

*Inflorescence diameter.*—About 4 to 5 cm.

*Inflorescence height.*—About 2.3 cm.

*Flowers.*—Appearance: Flared trumpet, corolla fused, four-parted; flowers roughly rectangular in shape. Diameter: About 1 to 1.2 cm. Corolla tube length: About 1 cm.

*Flower buds.*—Length: About 4 mm. Diameter: About 5 mm. Shape: Roughly spherical. Color: 46A to 46B.

*Corolla.*—Arrangement/appearance: Single whorl of four petals, fused into flared trumpet. Petal length from throat: About 6 mm. Petal width: About 6 mm. Petal shape: Orbicular. Petal apex: Blunt. Petal margin: Entire; ruffled. Petal lobe texture, upper and lower surfaces: Smooth, velvety. Corolla throat and tube texture: Pubescent. Color: Petals, when opening, upper surface: 21A. Petals, when opening, lower surface: 12A to 35A. Petals, fully opened, upper surface: 45B; color becoming closer to 45C with development. Petals, fully opened, lower surface: 58B.

*Calyx.*—Arrangement/appearance: One single calyx tube per flower. Sepal length: About 9 mm. Sepal width: About 2.5 mm. Apex: Two-pointed. Texture, upper and lower surfaces: Pubescent. Color, upper and lower surfaces: 137A.

*Peduncles.*—Length: About 5.5 cm. Diameter: About 1.5 mm. Angle: Upright. Strength: Flexible, but strong. Texture: Pubescent. Color: 144A.

*Pedicels.*—Not observed, flowers not stalked.

*Reproductive organs.*—Stamens: Quantity/arrangement: Four per flower, adnate to floral tube. Filament color: White, close to 155D. Anther shape: Ovoid. Anther length: Less than 1 mm. Pistils: Quantity: One per flower. Stigma shape: Globular. Fruit: Diameter: About 5 mm. Shape: Roughly spherical. Texture: Smooth. Color: 103A. Seed: Diameter: About 2.5 mm. Color: 200D.

Disease/pest resistance: Plants of the new Lantana have not been observed to be resistant to pathogens and pests common to Lantana.

Weather tolerance: Plants of the new Lantana have been observed to be very tolerant to rain and wind.

Temperature tolerance: Plants of the new Lantana have been observed to be tolerant to temperatures ranging from 0 to 38° C.

It is claimed:

1. A new and distinct cultivar of Lantana plant named 'Red Butler', as illustrated and described.

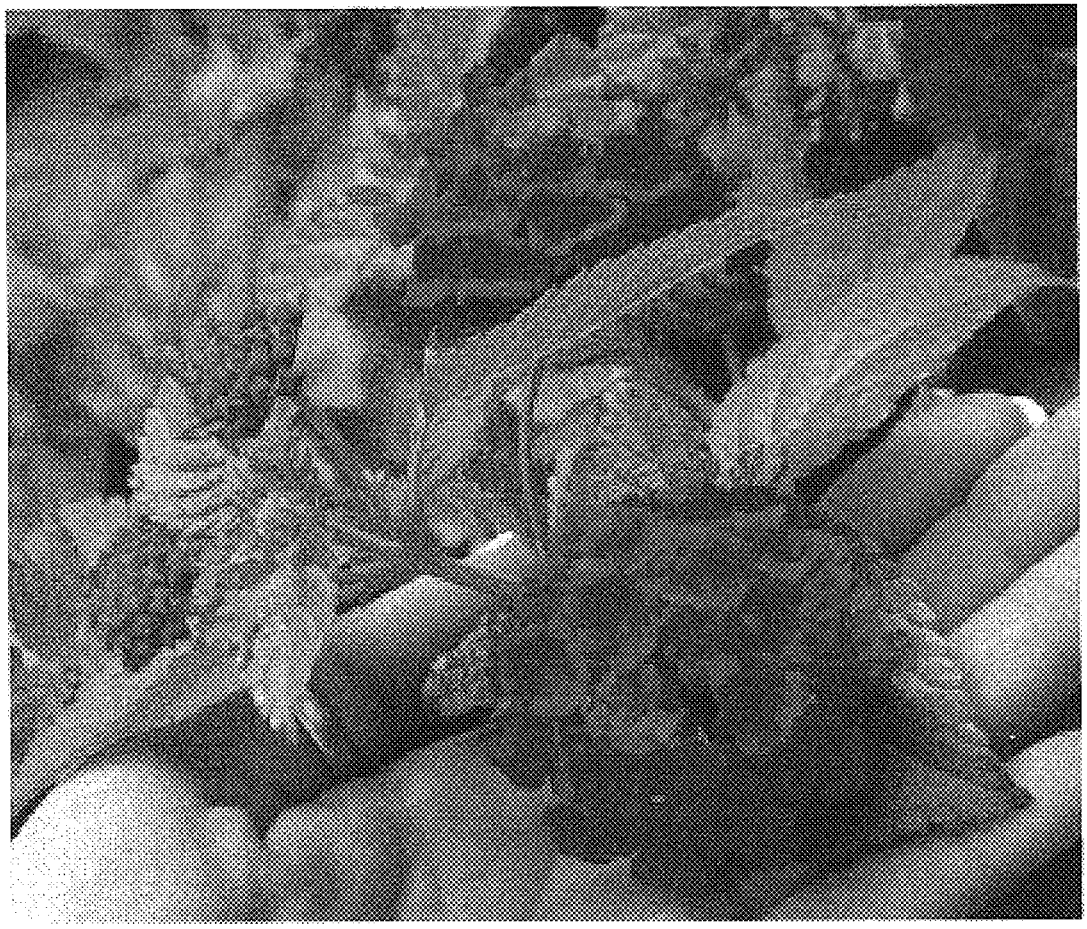

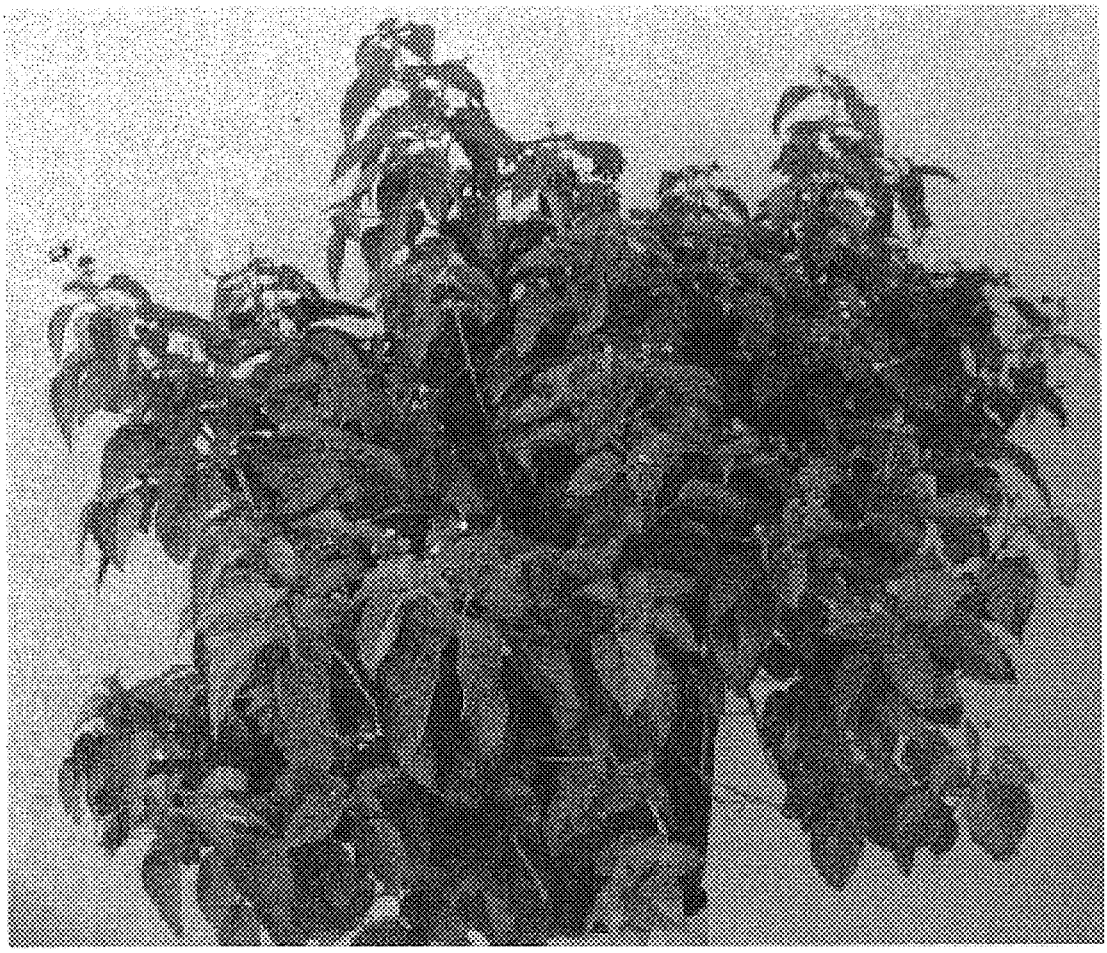

* * * * *